United States Patent [19]
Prestel et al.

[11] Patent Number: 5,746,750
[45] Date of Patent: May 5, 1998

[54] MEDICAL INSTRUMENT FOR MANIPULATION OF THE UTERUS

[75] Inventors: Stephan Prestel, Rheinstetten-Mörsch; Manfred Boebel, Ötisheim, both of Germany; Harry Reich, Kingston, Pa.; Hossein Messroghli, Gross-Gerau, Germany

[73] Assignee: Richard Wolf GmbH, Knittlingen, Germany

[21] Appl. No.: 795,031

[22] Filed: Feb. 5, 1997

[30] Foreign Application Priority Data

Feb. 5, 1996 [DE] Germany .................... 196 03 981.9

[51] Int. Cl.⁶ .................................................. A61B 17/42
[52] U.S. Cl. .................................... 606/119; 606/108
[58] Field of Search .......................... 606/119, 108, 606/1; 604/45, 55, 193, 197, 278, 279

[56] References Cited

U.S. PATENT DOCUMENTS

| | | |
|---|---|---|
| 4,000,743 | 1/1977 | Weaver . |
| 5,209,754 | 5/1993 | Ahluwalia . |
| 5,368,598 | 11/1994 | Hasson .................................... 606/119 |
| 5,382,252 | 1/1995 | Failla et al. ............................ 606/119 |
| 5,445,168 | 8/1995 | Krebs ..................................... 128/898 |
| 5,464,409 | 11/1995 | Mohajer ................................. 606/119 |
| 5,562,680 | 10/1996 | Hasson ................................... 606/119 |

FOREIGN PATENT DOCUMENTS

| | | |
|---|---|---|
| 0 400 458 A1 | 5/1990 | European Pat. Off. . |
| 0 615 727 A1 | 3/1994 | European Pat. Off. . |
| WO 94/00061 | 1/1994 | WIPO . |
| WO 94/10926 | 5/1994 | WIPO . |

*Primary Examiner*—Michael Buiz
*Assistant Examiner*—Tina T. D. Pham
*Attorney, Agent, or Firm*—Cohen, Pontani, Lieberman, Pavane

[57] ABSTRACT

A medical instrument is provided for manipulation of the uterus, in particular for laparascopic complete hysterectomy. It comprises a handle at the proximal instrument part and a manipulator probe at the distal instrument part, these being connected to one another via an elongate shank. Furthermore a holding device is arranged at the distal instrument part for fastening the uterus subject to therapy relative to the manipulator probe. In order to prevent the pneomoperitoneum from being destroyed during the operation to remove the uterus, the invention provides for a sealing device in the form of a closed tube insertable into the vagina, in which the shank of the instrument is axially displaceably arranged.

9 Claims, 6 Drawing Sheets

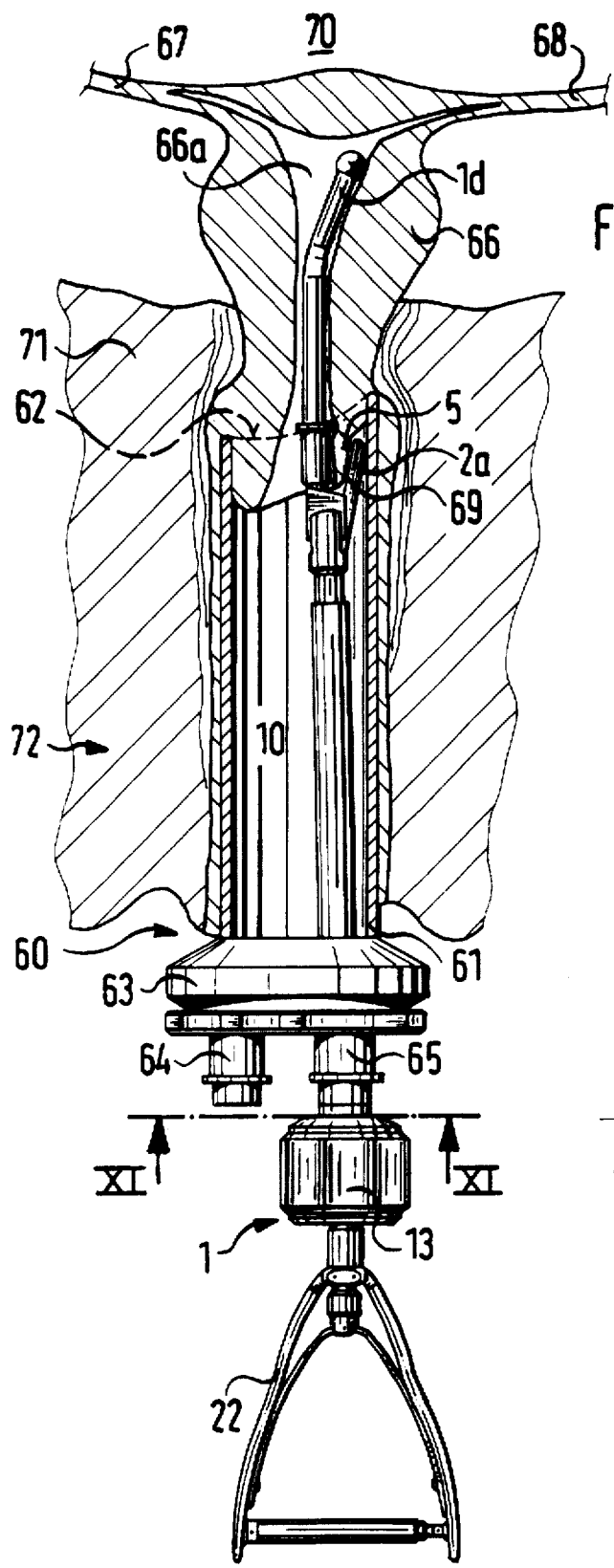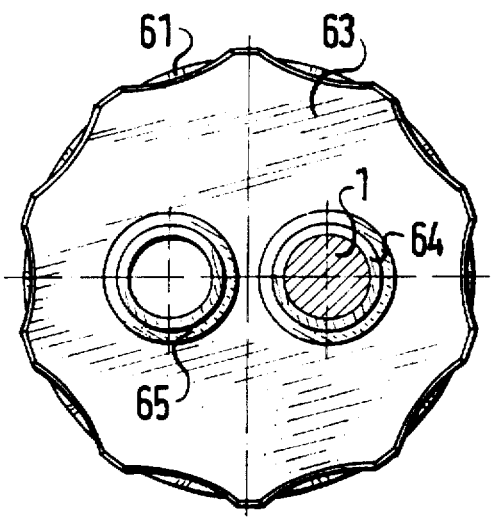
FIG. 10
FIG. 11

MEDICAL INSTRUMENT FOR MANIPULATION OF THE UTERUS

BACKGROUND OF THE INVENTION

1. Field of the Invention

The invention relates to a medical instrument for manipulation of the uterus, in particular for laparascopic complete.

2. Description of Related Art

Instruments of this type are for example used in laparascopic complete hysterectomy. With this, the instrument for manipulation of the uterus serves to tilt the uterus in various directions in order for example to be able to carry out the free dissecting of the uterus from blood vessels, ligaments and likewise. With such operation techniques an absolute as possible gas impermeability must be present. It is therefore necessary to provide a sealing mechanism on the vaginal side.

An instrument according to the preamble is known from WO 94/00061 which also describes the operation procedure per se in more detail. The instrument disclosed in WO 94/00061 comprises a round cross section of which the distal end is formed as a splaying device. After introducing the manipulator into the cavum uteri, the distal splaying device is splayed by operating the proximal handle and thus the uterus and manipulator are fixed to one another. In the distal region the manipulator comprises a bending device so that by bending the distal region and also by rotation of the instrument, the uterus is pivoted and turned into just that position required by the operator. During the laparascopic free dissection, the vagina is sealed to the outside using a flexible sealing device by which means the pneumoperitoneum may be maintained. After the free clerarance of the uterus, the sealing device is removed and with appropriately designed scissors, the freely dissected uterus is cut from the rear vaginal fornix and pulled out via the vagina. With this the pneumoperitoneum is lost and must be re-established after a renewed sealing on the vaginal side has been effected.

European Patent No. 0400458 and U.S. Pat. No. 4,000, 743 disclose uterus manipulators comprising a distal cone for sealing the uterus. At the proximal end of the instrument there is provided a holding device which comprises a receiver for fastening a holder (tenaculum). The holder fixes the guiding instrument relative to the uterus to be manipulated. After introduction of the guiding device through the vagina into the uterus, the cervix is gripped by a holder and fixed in a holding arm of the guiding instrument. A secure sealing of the vagina cannot be achieved with these instruments.

A uterus manipulator is described in European Patent No. 0615727 in which the distal end is able to be pivoted using a push rod. The distal probes which can be releasably fixed to this distal end may be designed in various ways, for example as cannulas or hooks, so that the uterus may be examined or undergo therapy, according to the attachment used, for instance in the case of a cannula the uterus may be treated with medication. Particularly due to the use of both the holding rod and operating rod, a reliable sealing of the vagina with such a uterus manipulator cannot be achieved.

SUMMARY OF THE INVENTION

It is the object of the present invention to design an instrument of the type according to the preamble such that it ensures the maintaining of the pneumoperitoneum once it has been set up and thus permits a shortening of the operation time.

Accordingly, a sealing device is provided which seals the instrument shank to the vagina, whereby the sealing device is designed such that the shank is axially displaceable therein. In this manner it is possible to maintain the pneuomoperitonium during the whole operation (with laparascopic complete hysterectomy), by which means the total duration of the operation can be considerably be reduced. With this, the stabilization of the position of the uterus for the free dissection is effected as hitherto using an instrument introduced on the vaginal side whereas the free dissection is effected in the hitherto known manner from the abdominal cavity. In comparison to the procedure according to the state of the art however, the sealing device according to the invention permits the maintenance of the pneumoperitoneum until the completion of the operation, since after the free dissection of the uterus, it is pulled by the instrument into the region of the vagina, whereupon from the abdominal cavity, a severing of the rear fornix of the vagina and an occluding of the opening resulting therefrom whilst maintaining the pressure on the side of the abdominal cavity is made possible.

The sealing device may be formed in a simple manner using a vaginal insertable tube having a transverse wall in which at least one recess for the sealed passing through of a shank is provided. The tube is preferably so formed such that alone due to its outer periphery, it guarantees a seating connection with the vagina. Furthermore it is useful to form the distal end of the tube rounded and having a diameter such that an as sealed as possible bearing on the cervix is effected (see FIG. 10). Such design of the tube does not require any further sealing means and further ensures an adequate free space for receiving the uterus to be removed.

Preferably two introduction connection pieces are provided within the transverse wall of the sealing device and these are preferably automatically closable similar to a return valve and ensure an as sealed as possible closure with an inserted shank as well as in the empty condition. The provision of introduction connection pieces in the transverse wall further has the advantage that a certain guiding function is ensured for the shank to be introduced, this simplifying the handling of the shank to be introduced or the already introduced shank.

In order to be able to reliably hold the uterus during its free dissection with little constructional effort, the invention provides for a holding device which is so designed such that a claw for gripping the cervix is pivotably arranged to the manipulator probe, with the manipulator probe together with the holding device being bendable to the axis of the instrument. Such a formation has a simple design and at the same time is advantageous for the handling. Only the manipulator probe is to be introduced into the uterus whereupon by operation of the holding device, a rigid connection to the instrument is produced. With the possibility of being able to bend this whole aggregate using a proximal control, the uterus may be brought into every position required for the free dissection.

The operation of the holding device is preferably effected using a pincer type grip arrangement, for example a flail type grip, whilst the angular position is controllable using a twist handle arranged at the proximal part of the instrument. Such a twist handle permits a delicate pivoting of the distal part of the instrument from the proximal region and permits self locking in a simple manner, so that no separate fastening mechanism is required.

In order to be able to ensure a secure fixing of the uterus, in particular the cervix, by way of the holding device on the one hand, but also on the other to substantially prevent any ripping of the tissue, it is useful to provide a spring arrangement between the handle and the holding device which limits the holding force. This means that on overstepping a certain holding force, the movement on the handle side is not transmitted any further to the holding device, but is compensated by the spring arrangement. Furthermore, an engageable catch may be provided which renders the spring arrangement ineffective, in order to permit a more delicate operation.

It is further advantageous if the instrument comprises a rinsing connection on the proximal side. By these means a simple and quick cleaning of the instrument is made possible.

It is useful when the manipulator probe comprises an exchangeable probe head, by which means a suitable shape or size of the probe head may be selected.

BRIEF DESCRIPTION OF THE DRAWINGS

The invention is hereinafter described in more detail by way of one embodiment example shown in the drawings. These show:

FIG. 10 a longitudinal section through a uterus, with an applied instrument and seal; and FIG. 11 a plan view of the proximal end of the seal.

DETAILED DESCRIPTION OF THE PREFERRED EMBODIMENTS

Figure 1:
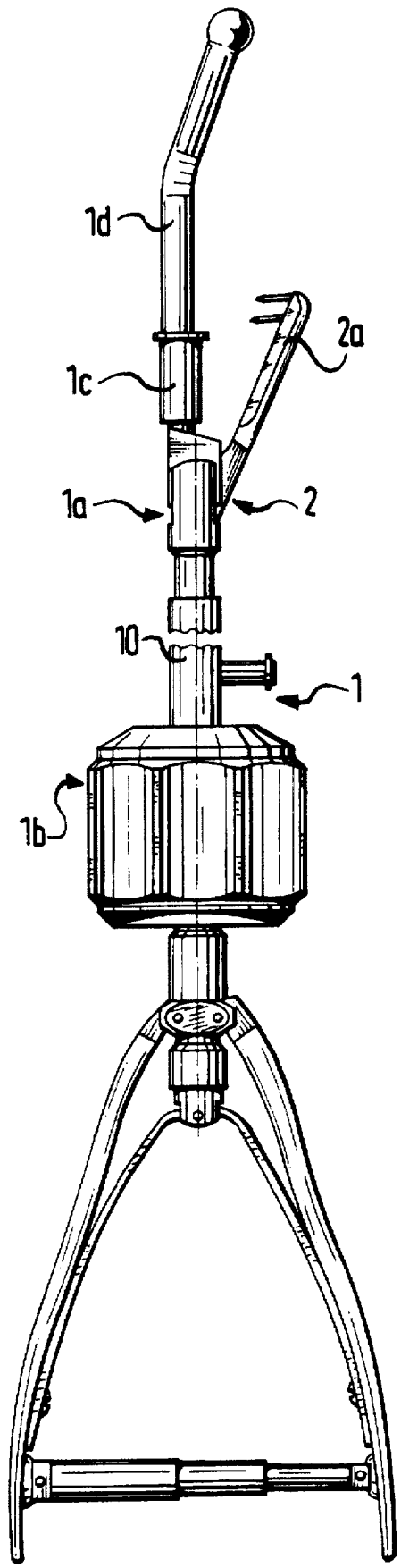
FIG. 1 a lateral view of the instrument according to the invention, in a simplified representation.
Figure 2:
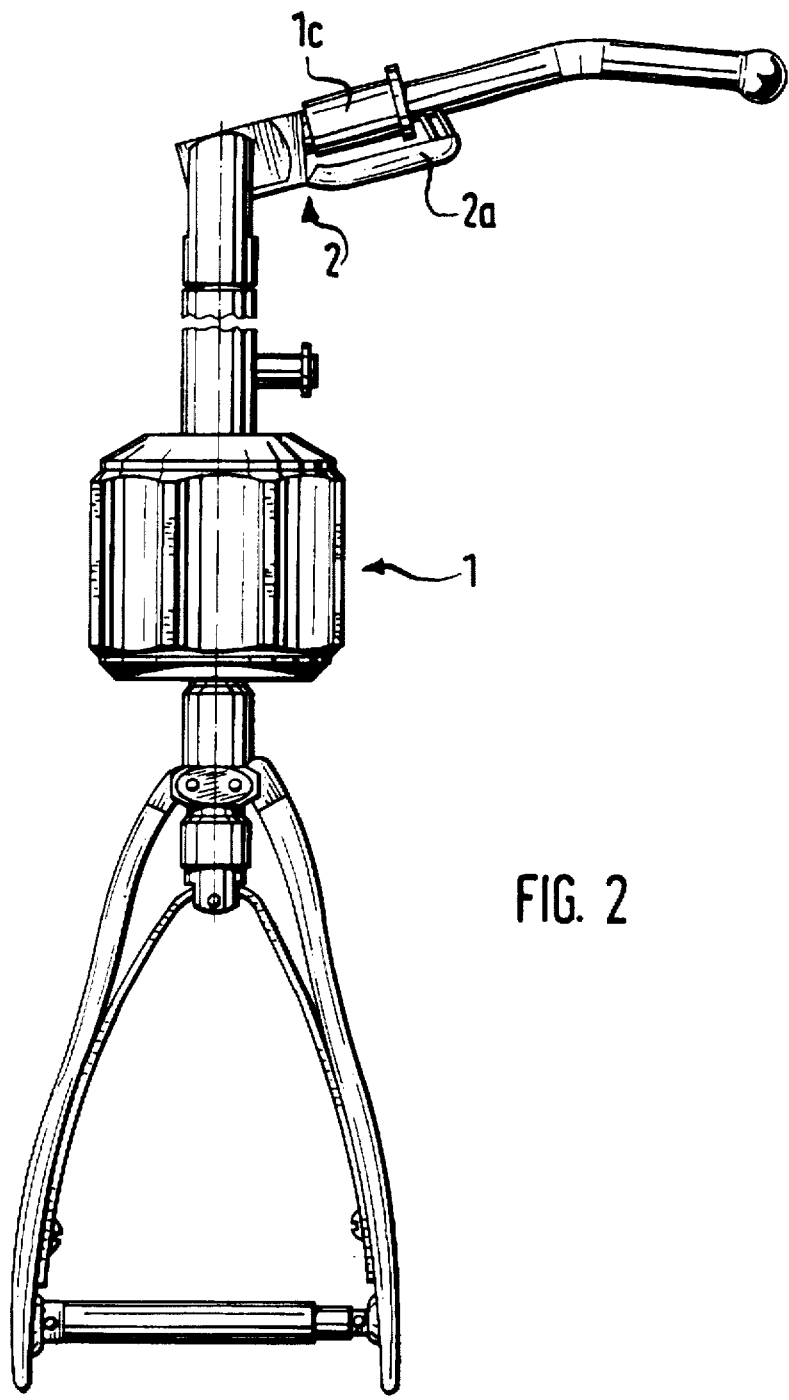
FIG. 2 a lateral view of the instrument according to the invention with a bent manipulator probe, in a simplified representation.
Figure 4A:
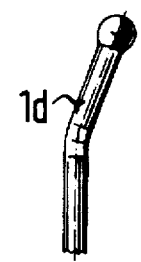
FIG. 4a a lateral view of a probe head of the manipulator probe of the instrument according to the invention.
Figure 4:
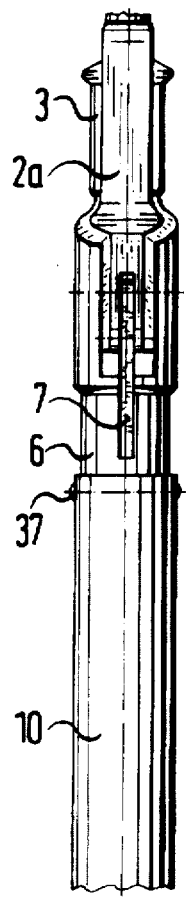
FIG. 4 a plan view of the distal end of the instrument according to the invention.
Figure 5:
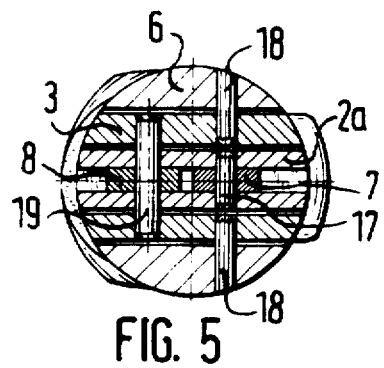
FIG. 5 a section taken along the section line V—V in FIG. 3.
Figure 3:
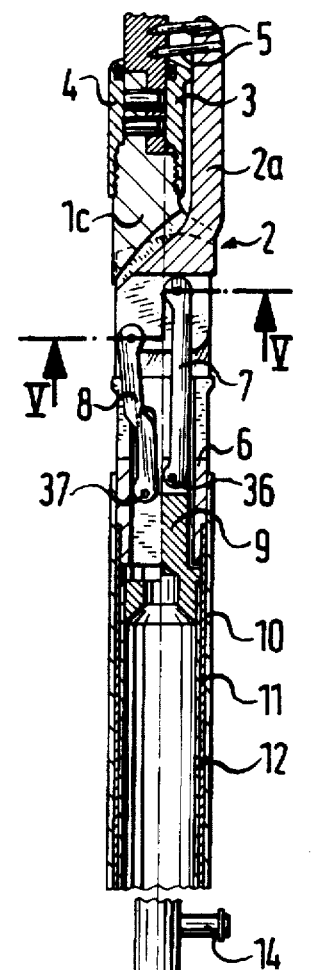
FIG. 3 a lateral view of the instrument according to the invention with an enlarged cross sectional representation of the distal end of the instrument.
Figure 3:
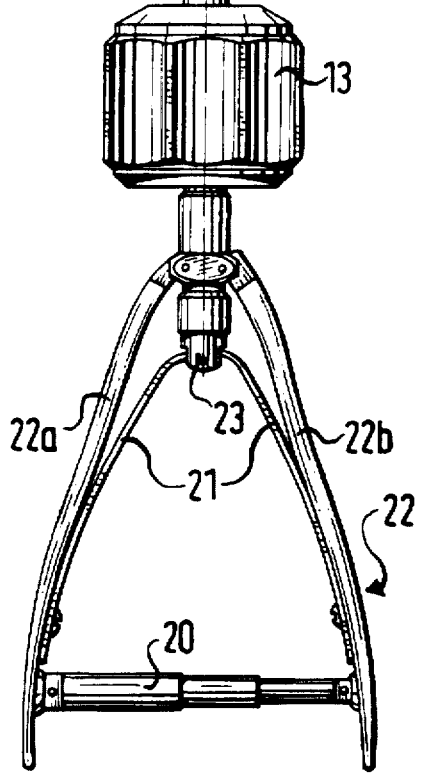
Figure 6:
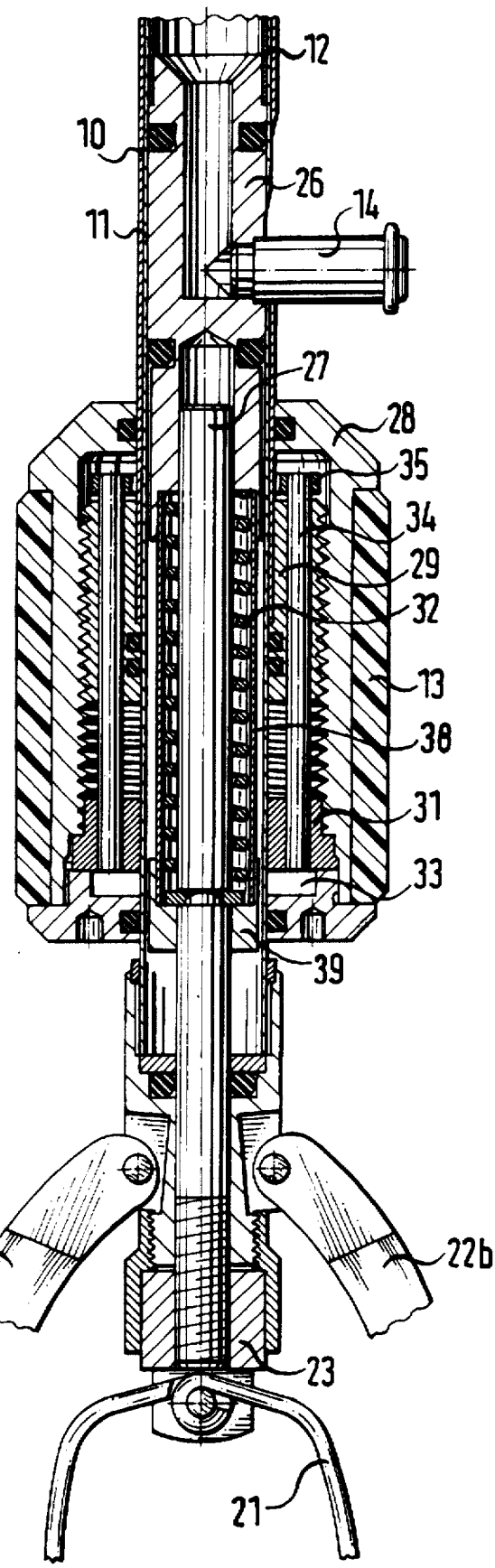
FIG. 6 a longitudinal section through the proximal part of the instrument.

The instrument 1 according to the invention represented in the figures comprises essentially of three functional groups, that is, the distal instrument part 1a, the proximal instrument part 1b and the instrument shank 10 connecting both these parts, which in the figures is represented shortened.

The distal instrument part 1a comprises a manipulator probe 1c which is bendable with regard to the shank 10 of the instrument 10 and which can be mounted by way of a holding nut 4, and a holding device 2. Instead of the holding nut 4, a push sleeve may be provided for mounting the probe 1c. The holding device 2 comprises a jaw piece 2a which can be pivoted against a jaw piece 3 of the manipulator probe 1c and into whose front end there are inserted pointed parts 5. The pointed parts 5 which may be of any shape serve to hook up the cervix 60 of a uterus 66.

The instrument shank 10 comprises three tubes 10, 11, 12 lying within one another. The tube 11 is distally rigidly connected to a holder part 6, in whose branches the jaw piece 3 of the manipulator probe 1c is mounted via pins 18. On operation of proximally mounted gripping limbs 22a and 22b of a flail type grip 22, a link piece 23 is axially moved via a spring pair 21. This link piece 23 is connected to a push rod 27 which axially moves the push rod tube 12 via a spring 32 and a connecting piece 26. A holding part 9, on which a lever 7 is pivotably mounted via a pin 36, is fixed to the push rod tube 12. The lever 7 is again pivotably connected to the jaw piece 2a via a pin 17. On moving the gripping limbs 22a, 22b of the flail type grip 22, the jaw piece 2a of the holding device 2 is opened and closed, there being a pin 19 serving as a pivot axis. With a catch 20, the gripping limbs 22a, 22b of the flail type grip 22 may be arrested in the closed condition. Various tissue strengths are compensated for by a spring system 26, 27, 32, 33, 38, 39. With a large resistance at the jaw piece 2a (corresponding to a strong tissue) the axial movement which is not taken up by the jaw piece 2a is compensated by the spring 32, by which means a closing of the catch 20 is possible in all cases.

By rotating the handle 13, 28 a threaded bushing 29 which is rigidly connected to the tube 10 is axially displaced on the tube 11. The threaded bushing 29 is secured against twisting by way of guiding keys 34 guided in longitudinal grooves. The guiding keys 34 are rigidly connected to a holding ring 35 and to a guiding ring 31. The guiding ring 31 is again rigidly connected to the forceps tube 11.

The axial movement of the tube 10 with respect to the tube 11 is transmitted via a pin 37 by a lever 8 and finally by a link pin 19. On rotation of the handle 13, the manipulator probe 1c with the holding device 2 is bent over the pivot point formed by the pins 18. In the closed condition of the jaw pieces 2a, 3, the pins 17 and 18 are flush with each other and the complete instrument part 1a may for example be bent over 70°, without the holding device 2 moving relative to the jaw piece 3. It can also be provided that the pins 17 and 18 lie flush to one another for a certain angle suitable for an application.

Figure 8:
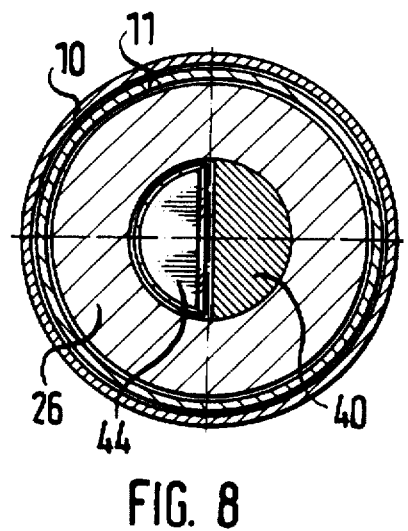
FIG. 8 a section taken along the section line VIII—VIII in FIG. 7.
Figure 9:
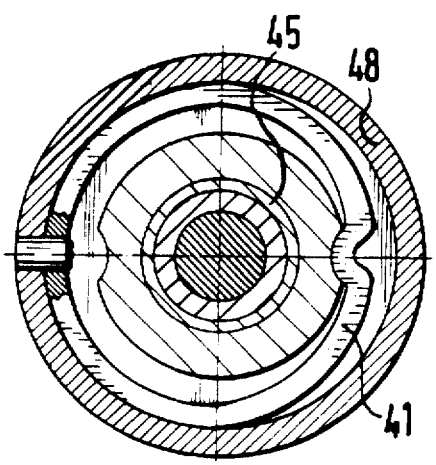
FIG. 9 a section taken along the section line IX—IX in FIG. 7.
Figure 7:
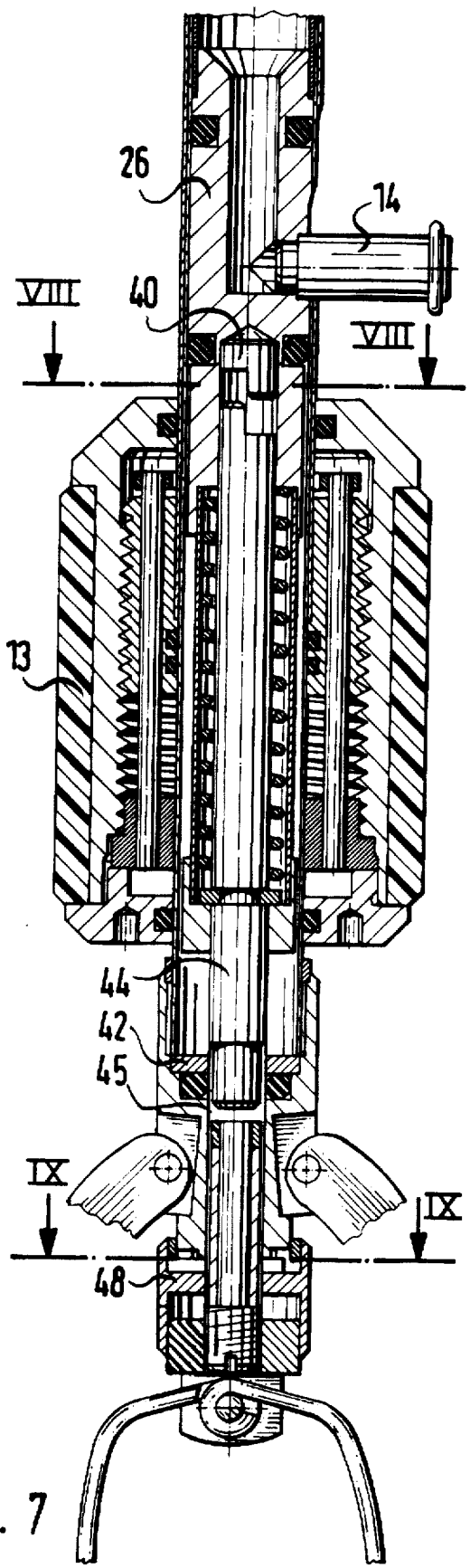
FIG. 7 a longitudinal section through the proximal part of the instrument in a second embodiment according to the present invention.

In a second embodiment represented in FIGS. 7 to 9 the spring system may be engaged or disengaged by rotating a wheel 48.

The wheel 48 is rigidly attached to the tube 45 and the push rod 44. On rotation of the wheel 48, the push rod 44 may be so positioned that the distal semi-circular end face of the push rod 44 strikes the end face of a stop 40 or is laterally led past the surface. The arresting of the wheel 48 is effected via the spring 41 and the grip receiver 42.

To the instrument shank 10 there is mounted a Luer connection 14 through which the inner hollow space of the instrument shank 10 is accessible for cleaning.

A sealing device 60 is shown in FIG. 10 with a tube 61 of the sealing device 60 being shown in a representation in which the tube 61 is already sealingly inserted into a vagina 72. The tube 61 is rounded at its distal end 62 corresponding to the particulars of the anatomy. On the proximal side, the tube comprises a transverse wall 63 in which, in the example shown, there are arranged two seal bonnets 64, 65 which serve as introduction sealing connection pieces. The instrument 1 is inroduced via one of the introduction sealing connection pieces 64, 65 and the manipulator probe 1c is already placed in the cavum uteri. The uterus is accorded the reference numeral 66 and the fallopian tubes 67 and 68. The pointed parts 5 of the jaw piece 2a of the holding device 2 are hooked into the cervix 69 which projects into the vagina 72 in a plug type manner. It is ensured by way of the sealing device 60 that the pneumoperitoneum is maintained in the abdominal cavity 70 during the whole operation. With the procedure using the instrumentation according to the invention, proceding from the abdominal cavity 70, the uterus is laparascopically freely dissected. After this has been carried out, the rear fornix of the vagina 71, likewise proceding from the abdominal cavity 70, is completely severed annularly around the uterus 66. Subsequently the uterus 66 is pulled into the tube 61 with the help of the instrument 1, and proceeding from the abdominal cavity, from which the severing of the rear fornix of the vagina is also effected, the resulting opening is closed, and again due to the sealing of the tube 61, the maintaining of the pneumoperitoneum is guaranteed.

What is claimed is:

1. A medical instrument for manipulation of the uterus through a vaginal opening of a vagina comprising:

an elongate shank having a proximal end, a distal end and a longitudinal axis;

a manipulator probe, disposed at the distal end, for manipulating the uterus;

a holding means, pivotally connected to the distal end, for fastening the uterus in at least one therapeutic position relative to said manipulator probe;

a handle, disposed at the proximal end, for holding said elongate shank;

a sealing means for receiving said elongate shank and for sealing said elongate shank within the vagina, such that when said sealing means is inserted into the vaginal opening and said elongate shank is inserted therethrough, said elongate shank is sealed within the vagina such that said sealed elongate shank is axially displaceable within said sealing means.

2. The medical instrument of claim 1, wherein said sealing means comprises:

a hollow cylindrical housing, for insertion through the vaginal opening, having a first end and a second end, such that when said cylindrical housing is inserted through the vaginal opening, said first end is disposed inside the vagina and said second end is disposed external to the vaginal opening; and a transverse wall, positioned across said second end, having at least one opening therethrough for sealably receiving said elongate shank.

3. The medical instrument of claim 2, wherein said hollow cylindrical housing is sufficiently dimensioned to form a seal in the vagina when said hollow cylindrical housing is inserted through the vaginal opening until said first end sealably engages a cervix of the uterus.

4. The medical instrument of claim 2, wherein said transverse wall comprises at least one connection device dimensioned to receive said elongate shank, each of said at least one connection devices being positioned at each opening of said at least one opening, said at least one connection device further comprising closing means for sealably closing said at least one connection device, and radial sealing means for sealing said elongate shank within the vagina when said shank is inserted through said at least one connection device.

5. The medical device of claim 1, wherein said holding means is mounted on said manipulator probe, and wherein said holding means further comprises at least one claw, pivotably mounted on said manipulator probe, for engaging a cervix of the uterus.

6. The medical device of claim 5, wherein said manipulator probe is pivotably mounted on said distal end, such that said manipulator probe is pivotable with respect to said longitudinal axis of said elongate shank.

7. The medical device of claim 6, wherein said handle further comprises a first control means for adjusting a first pivot angle of said at least one claw and for controlling a force exerted by said at least one claw on the cervix, and a second control means for controlling a second pivot angle of said manipulator probe.

8. The medical instrument of claim 7, further comprising spring means, connected to said first control means and to said at least one claw, for limiting the force exerted by said at least one claw on the cervix to a predefined limit.

9. The medical instrument of claim 8, further comprising means for engaging and for disengaging said spring means.

* * * * *